US012693188B2

(12) United States Patent
Fodor et al.

(10) Patent No.: US 12,693,188 B2
(45) Date of Patent: Jul. 28, 2026

(54) LEAKAGE DETECTION METHOD AND SYSTEM, IN PARTICULAR FOR USE IN A BLOOD TREATMENT DEVICE

(71) Applicant: B. Braun Avitum AG, Melsungen (DE)

(72) Inventors: Gábor Fodor, Budapest (HU); Ádám Szabó, Vác (HU); István Golarits, Budapest (HU)

(73) Assignee: B. Braun Avitum AG, Melsungen (DE)

( * ) Notice: Subject to any disclaimer, the term of this patent is extended or adjusted under 35 U.S.C. 154(b) by 314 days.

(21) Appl. No.: 18/472,404

(22) Filed: Sep. 22, 2023

(65) Prior Publication Data

US 2024/0102880 A1     Mar. 28, 2024

(30) Foreign Application Priority Data

Sep. 23, 2022    (EP) .................................... 22197547

(51) Int. Cl.
| *G01M 3/26* | (2006.01) |
| *A61M 1/16* | (2006.01) |
| *A61M 1/28* | (2006.01) |
| *A61M 1/36* | (2006.01) |

(52) U.S. Cl.
CPC ............ *G01M 3/26* (2013.01); *A61M 1/3607* (2014.02); *A61M 1/16* (2013.01); *A61M 1/1654* (2013.01); *A61M 1/28* (2013.01); *A61M 2205/15* (2013.01); *A61M 2205/50* (2013.01); *A61M 2205/52* (2013.01)

(58) Field of Classification Search
CPC .... G01M 3/26; A61M 1/3607; A61M 1/1654; A61M 1/28; A61M 1/16; A61M 2205/15; A61M 2203/3393; A61M 2205/50; A61M 2205/52

USPC ............................................................. 73/40
See application file for complete search history.

(56) References Cited

U.S. PATENT DOCUMENTS

| 6,481,980 B1 * | 11/2002 | Vandlik ................ F04B 49/065 |
| | | 417/313 |
| 7,618,542 B2 | 11/2009 | Okazaki |
| 9,089,639 B2 | 7/2015 | Breuel et al. |
| 10,888,649 B2 | 1/2021 | Garrido et al. |
| 2013/0150768 A1 | 6/2013 | Sakamoto et al. |
| 2016/0339156 A1 | 11/2016 | Gordon et al. |

(Continued)

FOREIGN PATENT DOCUMENTS

| CN | 110869068 B | 6/2022 |
| EP | 0321754 A1 | 6/1989 |

(Continued)

OTHER PUBLICATIONS

Communication pursuant to Article 94(3) EPC received in European Application No. 22 197 547.7-1113 dated May 31, 2024, 8 pages.

(Continued)

*Primary Examiner* — Peter J Macchiarolo
*Assistant Examiner* — John M Royston
(74) *Attorney, Agent, or Firm* — Christopher A. Rothe; CM Law

(57) ABSTRACT

A leakage detection method and system are used in blood treatment devices, such as a dialysis device used in continuous blood treatment/dialysis therapies, including renal replacement therapies.

16 Claims, 4 Drawing Sheets

(56)         References Cited

U.S. PATENT DOCUMENTS

2020/0114061 A1      4/2020  Burbank et al.
2021/0128806 A1*    5/2021  Mitrovic ............. A61M 1/1694
2022/0229028 A1*    7/2022  Rendl ..................... G01M 3/26

FOREIGN PATENT DOCUMENTS

EP            0611228  A2      8/1994
EP            0829265  B1      9/2001
EP            1543853  A1      6/2005
EP            2019296  A1      1/2009
EP            2670453  B1     12/2017
JP          2020151191 A       9/2020
WO            8501879  A1      5/1985
WO            9850091  A1     11/1998
WO          2004069311 A1      8/2004
WO          2012017959 A1      2/2012

OTHER PUBLICATIONS

Search Report received in European Application 22197547.7-1113
dated Feb. 17, 2023, 10 pages.
Communication under Rule 71(3) EPC received in European Appli-
cation No. 22 197 547.7-1113 dated Dec. 17, 2024, 8 pages.

* cited by examiner

LEAKAGE DETECTION METHOD AND SYSTEM, IN PARTICULAR FOR USE IN A BLOOD TREATMENT DEVICE

CROSS-REFERENCE TO RELATED APPLICATION(S)

This application claims priority under 35 U.S.C. § 119 to European Application No. 22 197 547.7, filed Sep. 23, 2022, the content of which is incorporated by reference herein in its entirety.

FIELD

The present disclosure relates to a leakage detection method and system, in particular for use in blood treatment device, e.g. in a dialysis device to be used in (continuous) blood treatment/dialysis therapies, in particular renal replacement therapies.

BACKGROUND

Blood treatment devices are widely known from the prior art. For example, EP 0 829 265 B1 discloses a blood treatment device that comprises an interface for a disposable tubing set, a plurality of pumps such as a blood pump, a syringe pump, an effluent pump and a substitution pump, load cells for measuring the weight of bags containing fluids required for the blood treatment, a user interface comprising a display with touch screen and a control unit for controlling the processes of the blood treatment device. In particular, this document discloses that the weight of fluid in a bag is determined using load cells and is compared to a target weight of fluid calculated from the flow rate. If the actual weight and the target weight differ, the fluid supply is controlled to reduce the difference between the actual weight and the target weight. Moreover, an alarm is triggered if the weight of the fluid in the bag does not match the expected weight.

In document US 2020/114061 A1 a leak sensing device for a medical device is shown. In this device—see passage [0028])—leakage can be detected without a leakage sensor by evaluating changes of pressure in a pressure line into which specific pressure signals are given.

From document US 2016/0339156 A1 a system and method for controlling operation of a negative pressure wound therapy apparatus has become known in which it is monitored whether a canister with a specific volume is full. For detecting a leakage in the system a response to a pressure pulse is used. This known system allows the status of the canister of a topical negative pressure (TNP) system to be determined without the necessity to provide two pressure sensors in the TNP system. By monitoring the magnitude of pressure 'pulses' created by a pump possible leakage or the fact that a canister filter may be full can be detected. Optionally two or more sensors can be used if very prompt detection of errors is desired.

WO 1985 001 879 A1 also discloses a dialysis device with load cells for weighing the contents of a bag. In particular, the weight of the bag is to be monitored in order to detect a system failure. An alarm is generated in a case where a weight loss is not indicated although it is present and should therefore be indicated, which according to the disclosure can be the case with a kinked bag.

In EP 0 321 754 A1 a procedure for monitoring hemo-diafiltration is described in which an initial test of an ultrafiltrate pump on the one hand and a scale on the other is made with the help of a monitoring device. The ultrafiltrate pump delivers a certain amount of ultrafiltrate on the scale and the weighing result is submitted to the monitoring device. Based on the known pumping chamber volume and the number of clocks the control unit calculates the pumped quantity and compares the calculated result with the weighing result. Only if both values match, the hemodiafiltration can be started. This method aims at monitoring the performance of the pump since in these days their flow rates varied in arrange of up to □ 10%.

From document EP 2 019 296 A1 a blood treatment device is known in which weight measuring devices at containers are connected to a control unit for calculating temporal change amounts of the weight of such containers. Based on the change amount of the weight a flow rate in the fluid line between pump and container is calculated. The pump is controlled such that it keeps the calculated flow rate of the respective fluid to be a predetermined flow rate.

EP 1 543 853 A1 discloses a blood purifying apparatus with multiple reservoir containers which are equipped with the weightmeters, respectively, so that data can be supplied from the individual weightmeters to a control unit. The control unit monitors the data from the weightmeters at all times and calculates the actual flow rate based on a change in weight per unit time. If it finds a difference between the actual flow rate and a set flow rate, the control unit automatically adjusts the rotation speed of a motor in each of the transfer pumps individually, such that the set flow rate equals the actual flow rate so as to maintain a flow rate accuracy. A similar system is known from WO 98/50091 A1.

In WO 2004/069311 A1 (EP 1 590 017 A1) a blood treatment system having various pumps and bags is known. In order to determine the amount of fluid released or collected in a particular bag or container the control unit compares at regular intervals (the greater the flows the smaller the intervals) the actual weight of the container with the desired weight (which is a direct function of the desired flow for each pump and of the time interval between each control step). The desired weight can be calculated as a function of the required flow (stored in a suitable storage unit of the computer) and of the time elapsed from the beginning of the treatment. If the actual weight and the desired weight differ from each other, the control unit acts on the corresponding pump so as to reduce, and possibly cancel, said difference. A similar system is described in EP 0 611 228 A2.

EP 2 670 453 B1 describes a method and system for controlling an extracorporeal blood treatment apparatus in which several pumps are controlled based on the measured change of weight of the associated containers. The weight reduction or weight increase of at least one of the containers is measured in the time interval in which the pump assigned to the respective container performs a preset number of revolutions or pumps strokes. Moreover, the delivery quantity of the respective pump at the preset number of revolutions or pump strokes is ascertained from the measured weight reduction or weight increase in the specific time interval, and the setpoint delivery quantity of the pump at the preset number of revolutions or pump strokes adopted in the drive of the respective pump is compared with the measured delivery quantity of the pump at the preset number of revolutions or pump strokes. After that, the drive of the pumps is based on the deviation of the adopted setpoint delivery quantity of the respective pump at the preset number of revolutions or pump strokes from the measured delivery quantity of the pump at the preset number of revolutions or pump strokes.

A problem in such known systems is to be seen in that the treatment accuracy (fluid removal accuracy in particular) is deteriorated by leakage in fluid containing or transporting medical disposables, such as containers, fluid lines and cartridges.

There are approaches in the prior art for solving this problem. WO2012/017959 A1 discloses a blood purifying device, and method for inspecting for liquid leakage therein, in which leakage is detected by using active pressurization of closed circuits of the device and monitoring the pressure development.

Other systems, e.g. the dialysis machine of CN110869068 B, use separate electronic leakage detectors.

SUMMARY

It is therefore the object underlying the present invention to provide a method and system for detecting leakage in fluid containing or transporting disposables, such as containers, lines or cartridges, which allows quick, easy and accurate leakage detection with a minimum of structural preparation.

Just by continuously monitoring the filling degree, e.g. the weight, of the container which is filled or drained through a fluid feed line by the pump controlled by a control unit (CPU), and by using known performance data of said pump, e.g. set rotation speed, segment or stroke volume and frequency, the set flow rate in the feeding line can be determined or calculated, resp., wherein in such calculation a correction can be carried out by considering characteristics of the hydraulic system of pump, feed line and container, such as pressure losses in the pump and/or in the feed line and/or influences of hydrostatic pressure changes due to changing filling degree of the container. Such characteristics can be taken into account and input into the system by depositing in the control unit look-up-tables (LUT) with data from previously measured or calculated characteristics. This calculated/determined flow rate is taken as the basis for calculating/determining an expected change rate value of the filling degree of said at least one container. Since the filling degree of the container is continuously monitored, the control unit knows the monitored change rate of the filling degree. By continuously comparing the expected change rate value or a previously monitored change rate and the current monitored change rate of the filling degree, i.e. by monitoring a deviation value, leakage can be detected, since such deviation value cannot be associated with any other known event, e.g. change of set flow rate. This means that any deviation value is not caused by the pump but is due to external effect, i.e. leakage from the fluid feed line including a pump segment (as a rule inserted into the pump) or the container.

For carrying out this improved method the system is equipped with a filling degree monitoring device configured to continuously monitor and report the filling degree of said container to the control unit (CPU), a first calculation/determination module configured to calculate a flow rate in said at least one fluid feed line based on the current performance of the at least one pump and optionally on selected characteristics of the hydraulic system including pump, feed line and container, a second calculation/determination module configured to calculate an expected change rate value of the filling degree of said at least one container based on said calculated at least one flow rate, an evaluation module configured to continuously monitor the deviation value between said expected change rate value and a monitored change rate of the filling degree of said at least one container, and output means configured to output a leakage signal based on said deviation value.

This concept can be applied to any unit of a fluid circuit configuration in which at least one pump fills or drains at least one container, as long as such pump is controlled by a control unit and the characteristics of such pumps and associated fluid feed lines are known, either measured or calculated.

In an advantageous manner, the method and system can be used to reliably detect leakages in blood treatment devices for e.g. blood treatment therapies, such as in acute dialysis machines.

The filling degree of a container of the method and system can be monitored by any suitable arrangement, e.g. optically or mechanically. It is advantageous, however, to monitor the filling degree of the container by continuously measuring the weight of said container, since in many known blood treatment machines bags or containers for different fluids are associated with load cells.

It turns out that sufficiently accurate results in detecting leakages can be obtained if the characteristics of the fluid system include data relating to at least one influence input out of the group of energy losses over fluid speed, mechanical parameters of the pump over pump performance and on hydrostatic pressure at a connection port of the pump.

Preferably, such data on characteristics of the fluid system are taken from a look-up-table (LUT) stored in the control unit (CPU) and based on measured and/or calculated characteristics of the hydraulic system including pump, feed line and container.

In order to avoid false leakage detections, it is advantageous that a leakage signal is only output if the above-described deviation value is for a pre-determined time interval above a pre-determined threshold value. In this way, deviations in specific situations, e.g. when external forces act on the fluid system for a short time, can be disregarded. Moreover, by this feature short term signal transient on the measured weight can be disregarded that superimposes to the otherwise expectedly changing data.

An advantageous application of the leakage detection method and system is a system working with fluid containing or transporting disposables, such as containers, lines or cartridges, in particular of medical disposables in particular for use in blood treatment devices for e.g., blood treatment therapies. In such systems as a rule a plurality of CPU-controlled pumps for blood, dialysate, substitution liquids and for effluents are used with fluid lines so that by applying the leakage detection method to such systems a substantial percentage of the overall fluid circuit can be monitored, thereby substantially raising the treatment safety for the patient.

An advantageous implementation of the new method is for example acute dialysis machine in which the at least one pump is:

a) a citrate pump and the container is an anticoagulation agent, e.g. citrate bag equipped with a load cell; or b) a substitution solution pump and the container is a substitution solution bag equipped with a load cell; or c) an effluent pump and the container is an effluent collecting bag equipped with a load cell; or d) a dialysis fluid pump and the container is a dialysis fluid bag equipped with a load cell.

The leakage detection system and method are applicable for all configurations in which a performance-controlled pump is connected via a supply or drain line to at least one container equipped with a filling degree, e.g. a weight detector. The system might contain an arbitrary number of pumps controlled by the control unit (CPU) to deliver fluid inside the lines into or out of a common container. In this case information on the performance, e.g. rotation and/or stroke volume of the pump is available to the control unit (CPU) since the performance is controlled and/or measured/ monitored by means connected to the control unit (CPU).

The system might also contain an arbitrary number of containers into or out of which a pump controlled by the control unit (CPU) delivers fluid. The expected weight change of the containers over time, i.e. the expected summed up weight change rate is calculated based on the set flow rate of the pump, which again is calculated from the pump performance (rotation, stroke volume, etc.) and—if required—characteristics of the hydraulic system including information about energy losses in fluid feed lines and pump and/or influence of absolute pressure variations. When there is no leakage in the hydraulic system (fluid lines, container, etc.) the sum of measured weight changes of the containers, i.e. the summed up real weight change rate over time corresponds to the expected summed up weight change rate. The measured weight change rate is continuously monitored. Thereby, leakage is detected whenever a change in the measured weight change rate is detected that cannot be associated with any known event, e.g. a change of the set flow rate, etc. This means that the measured weight change is not caused by the pump but is due to an external effect, e.g. leakage from the fluid lines or the containers.

When the at least one bag containing liquid to be pumped in or drained out is equipped with a filling level detector which is configured to report a filling level signal to the control unit (CPU) it is possible to consider changes of the hydrostatic pressure at a connection port of said at least one pump with the associated fluid feed line when calculating the expected weight change rates. With this modification the accuracy of leakage detection is additionally raised.

BRIEF DESCRIPTION OF THE DRAWINGS

The disclosure is further explained in the following with reference to figures of which.

The figures are merely schematic in nature and serve exclusively for understanding the present disclosure. The same elements are marked with the same reference signs.

DETAILED DESCRIPTION

Figure 1:
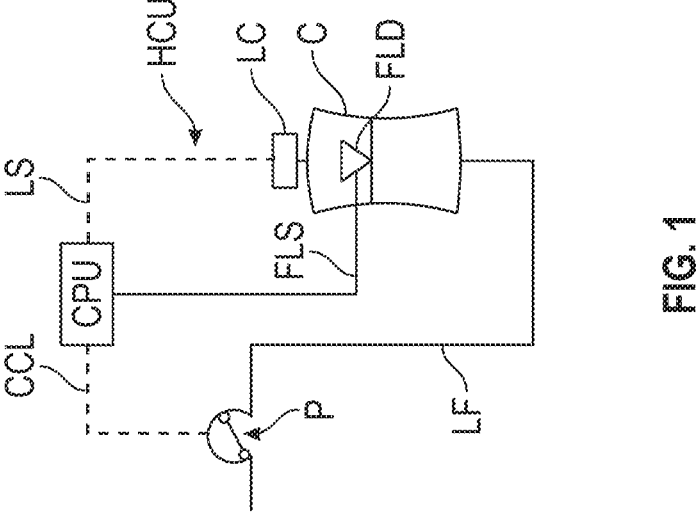
FIG. 1 is a schematic view of a hydraulic system unit in which a leakage detecting method according to the present disclosure can be carried out.

FIG. 1 shows a hydraulic circuit unit HCU in which a leakage detection method can be carried out. Such HCU can be implemented in any fluid circuits, e.g. in fluid circuits of fluid containing or transporting disposables, such as containers, lines or cartridges, in particular in medical disposables to be used in blood treatment devices for e.g. blood treatment therapies. The hydraulic circuit unit HCU consists of a pump P, e.g. a peristaltic pump, which can be bi-directionally driven and which is controlled via control circuit line CCL by a control unit, e.g. a CPU, a container C containing a fluid, a feed line LF connecting the pump P with the container C, and a monitoring unit for continuously monitoring the filling degree of the container C. In the shown one embodiment the monitoring unit consists of a load cell LC by which the weight of the container is continuously detected, and a signal line LS by which the detected value of weight (filling degree) is reported to the control unit CPU.

Figure 2:
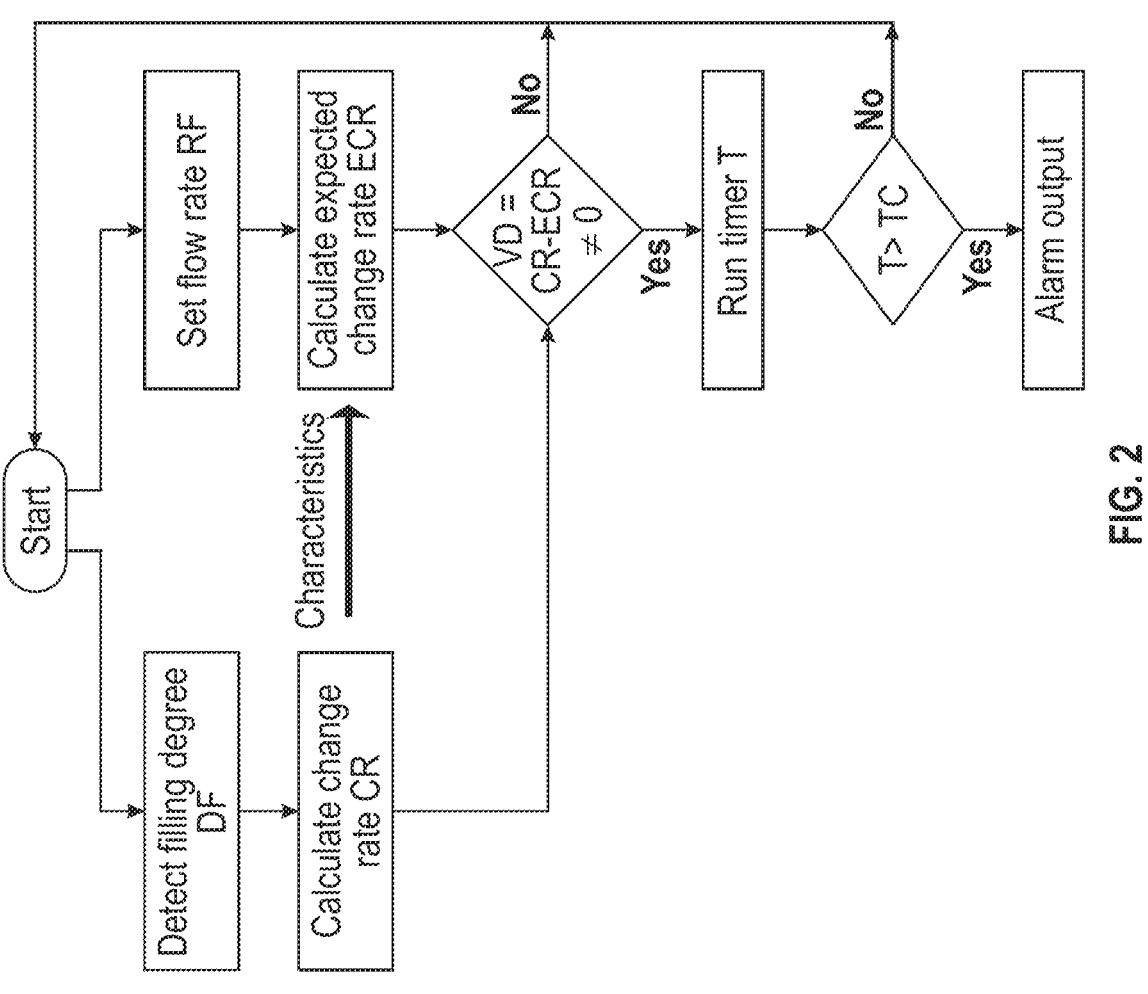
FIG. 2 is a flow chart illustrating the process steps of the leakage detecting method.

Such control by the CPU means that the CPU monitors the pump performance and sets the pump performance, i.e. output over time to a controlled value. The CPU uses data of the pump construction (pump chamber or stroke volume) and rotation or pump sequence so that the CPU can set and monitor any desired flow rate. Information on the rotation of the pump is also available to the CPU since the rotation is controlled and/or measured/monitored by control means connected to the CPU. For detecting leakages in the hydraulic circuit unit HCU the method works as illustrated in FIG. 2.

The filling degree DF, e.g. the weight of the fluid container C is continuously monitored so that the control unit CPU can continuously calculate a filling degree, e.g. a weight change rate CR.

Based on a set performance rate of the pump P, known by the running speed, e.g. rotation or stroke frequency, and constructional data of the pump a set flow rate RF in feed line LF can be calculated or determined. If required by the degree of accuracy, in this calculation characteristics of the hydraulic system of pump P, feed line LF and container C are considered, since—as a rule— a) the delivery rate of a pump P, e.g. a peristaltic pump, is depending on the speed of the pump since with increasing fluid speed energy losses increase, b) the delivery rate of the pump P depends on speed due to mechanical parameters, e.g. configuration of tube segments of a peristaltic pump, c) flow losses in the fluid lines LF increase with flow speed, d) energy losses depend on the hydrostatic pressure in the system, which again is depending on the filling level in the container C.

For taking the hydrostatic pressure of the system into account, the at least one container (bag) is equipped with a filling level detector (FLD) which is configured to report a filling level signal (FLS) (dotted control line in FIG. 1) to the control unit (CPU), wherein said signal is used to compensate the influence of changes of the hydrostatic pressure present at a connection port of said at least one pump P with the associated fluid feed line LF when calculating the expected weight change value(s).

These dependencies are taken into account by means of predefined look-up-tables (LTU) stored in the control unit (CPU) and based on measured and/or calculated characteristics of the hydraulic system including pump P, feed line LF and container C. These characteristics are used—if required—to compensate the measured delivery rates prior to the change of the pump rotation/stroke speed.

With this known pump flow rate an expected change rate value ECR of the filling degree of the container C can be calculated by the control unit CPU. In fixed time intervals, the values for the measured weight change rate CR and the expected change rate value ECR of the filling degree of the container C are compared. As long as these values do not substantially differ from each other, i.e. as long as the condition $$VD=CR-ECR=0$$

is fulfilled, i.e. a deviation value VD is ZERO, there is no leakage in the hydraulic circuit unit HCU of pump P, feed line LF and container C and the control system returns to START. Since any deviation between the values of CR and ECR cannot be associated with any known event, e.g. change of set flow rate caused by the pump, it is due to an external effect, i.e. leakage from the feed line LF or container C.

Alternatively, instead of using the deviation of calculated/ determined expected change rate and the measured change rate, the deviation value can be taken from the difference between a current and a previous value of monitored change rate (CR) of the filling degree (weight) of said at least one container (C). This alternative method can be applied when the desired accuracy/sensitivity in leakage detection could not be achieved due to the tolerances of performance data of pump (e.g. segment volume) based on which the flow rate in the feeding line is calculated.

As can be taken from the flow chart of FIG. 2, if a deviation value VD differs from ZERO, a timer for time T starts and the control unit (CPU) runs the timer as long as the deviation value VD continues to differ from ZERO. Only if the running time T is longer than a critical threshold time TC, the system outputs an alarm signal. By this modification deviations in special situations, e.g. short time disturbances, can be disregarded to avoid false leakage detection. Also, in this way short term signal transient on the measured weight can be excluded from the detection method, which would superimpose to the otherwise expectedly changing data.

Figure 3:
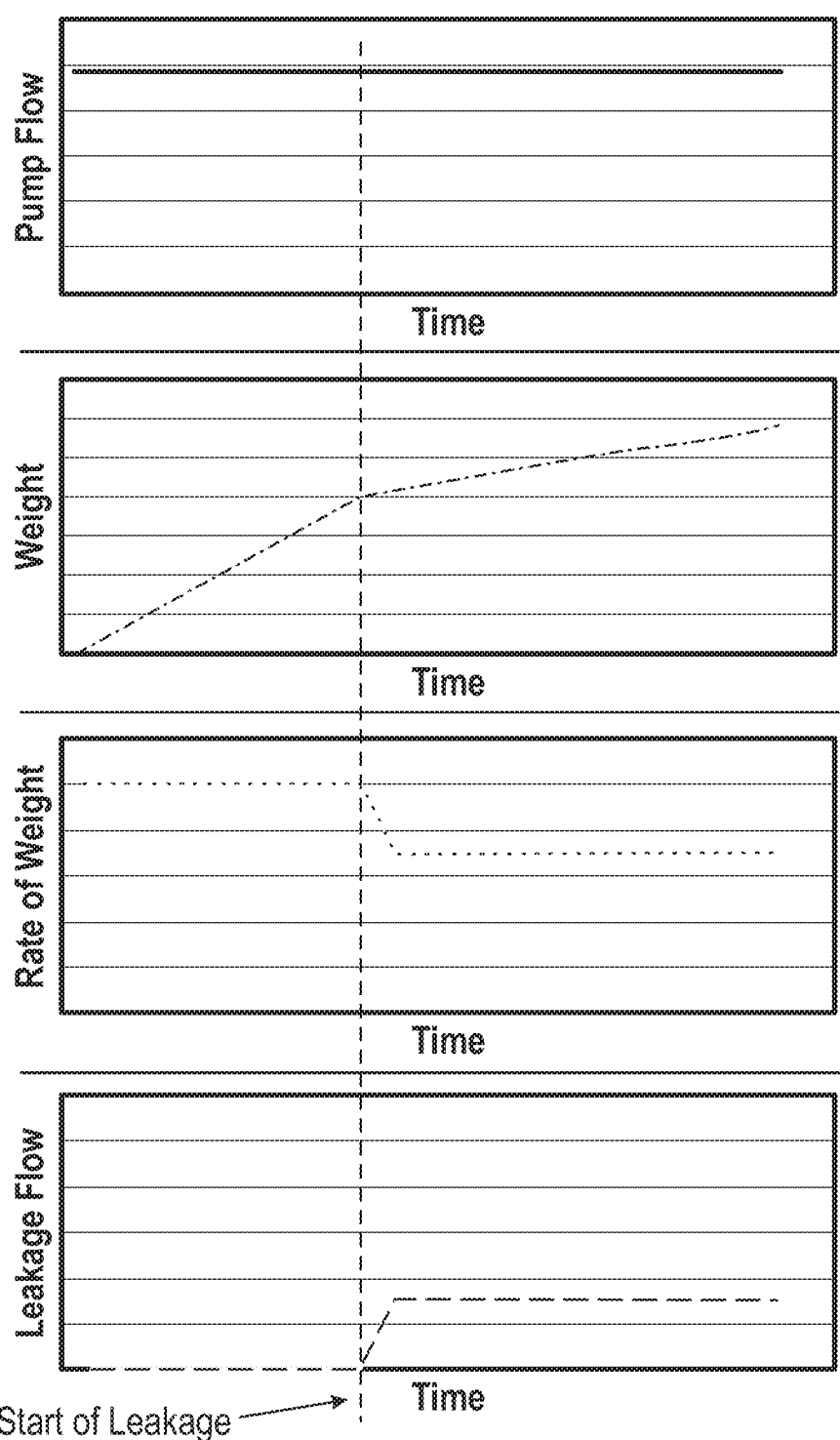
FIG. 3 is a diagram illustrating signals obtained when operating a hydraulic system and applying the leakage detection method according to the present disclosure.

FIG. 3 shows the signals which the control unit (CPU) receives and works with when operating the afore described leakage detection method. The four time diagrams show over time the set pump flow, the continuously measured weight of the container C, the change rate CR of weight of the container and a leakage flow. As can be seen, with a constant pump flow, the weight of the container C increases constantly, so that the weight change rate CR is constant, as long as there is no leakage in the hydraulic circuit unit HCU. In this situation the expected weight change rate ECR exactly matches with the measured weight change rate CR. As soon as leakage starts (indicated by bold arrow), the weight change rate CR drops so that the system reports a deviation value VD between the values of ECR and CR.

With other words, the leakage detection method is based on a continuous determination of an expected weight change rate ECR expected from the pump performance and option- ally from characteristics of the hydraulic circuit unit HCU including pump P, feed line LF and container C filling degree. By continuously monitoring the measured delivery or draining rate by the pump P through the feed line LF, the deviation between the expected (ECR) and the measured (CR) weight change rates can be continuously monitored. By this, potential leakage is detected based on the change of deviation between the expected and the measured delivery rate.

Figure 5:
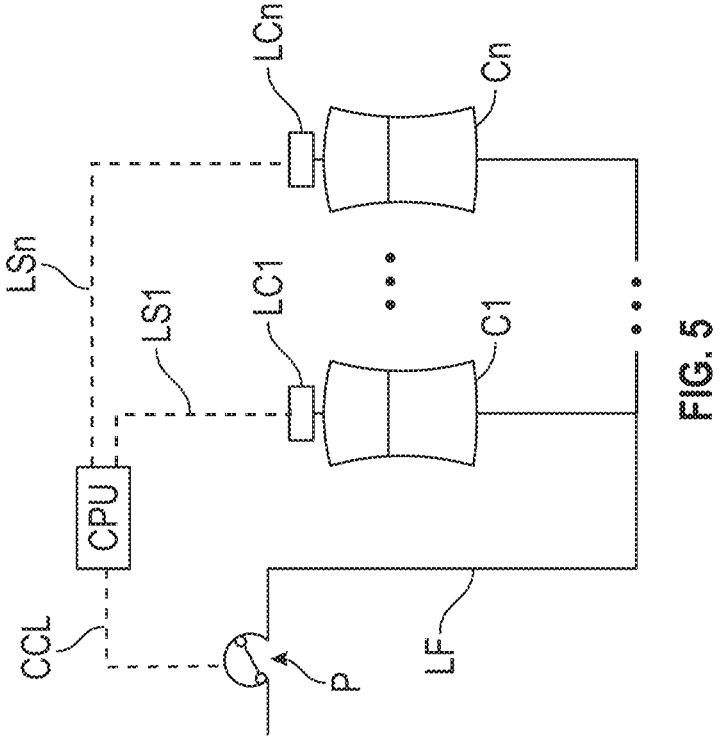
FIGS. 4 and 5 are schematic views similar to FIG. 1 and showing modifications of the hydraulic system unit in which a leakage detecting method according to the present disclosure can be carried out.
Figure 4:
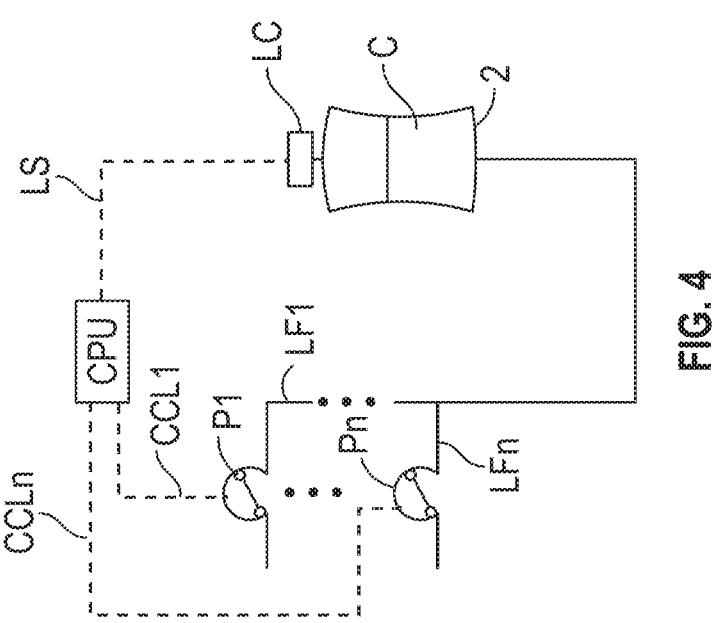

FIGS. 4 and 5 show modifications of the leakage detection system.

The system—as shown in FIG. 4—might contain arbi- trary number of pumps P1 to Pn, controlled by the control unit CPU to deliver fluid inside the lines LF1 to LFn into or out of a common container C. Information on the rotation of each pump is also available to the CPU since the perfor- mances of the pumps P (e.g. rotation) is controlled and/or measured/monitored by the means, illustrated by control circuit lines CCL1 to CCLn connected to the CPU.

The system—as illustrated in FIG. 5—might contain arbitrary number of containers C1 to Cn into or out of which a pump P, controlled by the CPU, delivers fluid by feed line LF. The weight of each container C1 to Cn is monitored by measuring means, i.e. load cells LC1 to LCn connected to the CPU by signal lines LS1 to LSn.

The sum of expected weight changes of the containers C1 to Cn over time (expected weight change rates) are calcu- lated based on the set flow rate (calculated from the rotation of the pump and the characteristics of the line(s). When there is no leakage in the system (lines, container, etc.), the sum of measured weight change of the containers C1 to Cn (real weight change rate) over time corresponds to the expected weight change rate. The measured weight change rate is again continuously monitored and summed up.

Leakage is detected, when a change in the measured weight change rate is detected, that can't be associated with any known event (e.g. change of set flow rate, etc.). This means that the change is not caused by the pump, but is due to an external effect—e.g. leakage from the lines or the container.

As becomes clear from the above, the above-described method is operated by a system in which the method steps can be carried out. The system is equipped with a filling degree monitoring device, in the described embodiment load cells LC, configured to continuously monitor and report the filling degree of said container C to the control unit (CPU), a first calculation/determination module—implemented in the CPU—configured to calculate a flow rate in said at least one fluid feed line LF based on the current performance of the at least one pump P and selected characteristics of the hydraulic system including pump P, feed line LF and container C, a second calculation/determination module—imple- mented in the CPU—configured to calculate/determine an expected change rate value ECR of the filling degree of said at least one container C based on said calculated at least one flow rate, an evaluation module configured to continuously monitor the deviation value VD between said expected change rate value ECR and a monitored change rate CR of the filling degree of said at least one container C, and output means configured to output a leakage signal based on said deviation value.

The above-described leakage detection method and can be implemented in an advantageous way into systems of fluid containing or transporting disposables, such as containers, lines or cartridges, in particular of medical disposables in particular for use in blood treatment devices for e.g., blood treatment therapies. An example of such implementation is shown in connection with FIG. 6.

Figure 6:
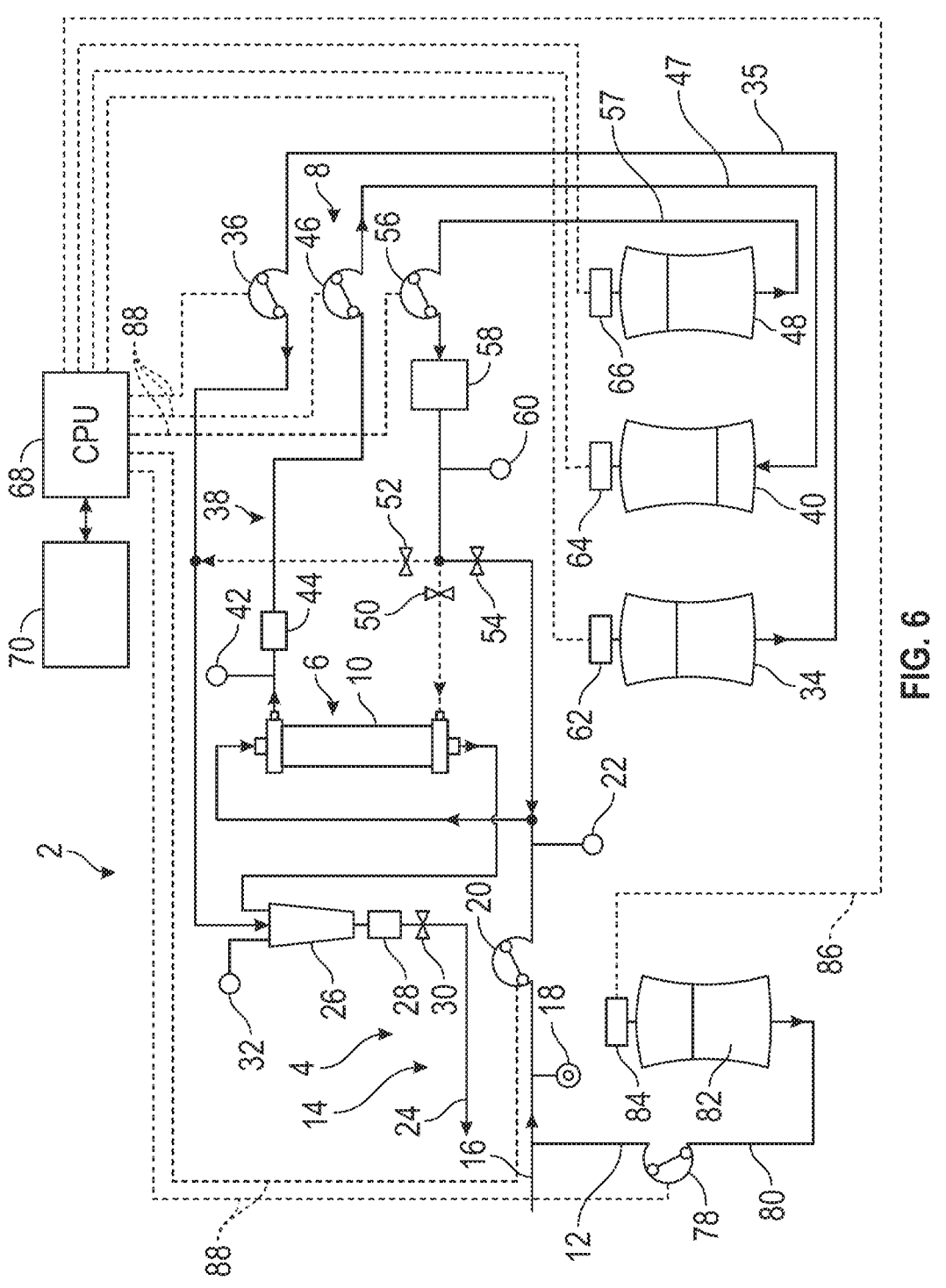
FIG. 6 is a schematic view of an extracorporeal blood treatment device in which the leakage detection method according to the present disclosure is implemented.

FIG. 6 is a schematic view of an extracorporeal blood treatment device 2 in which the above-described leakage detection method according to the present disclosure is implemented. The blood treatment device 2 is basically configured to be used in both continuous and intermittent blood treatment therapies, in particular renal replacement therapies. The blood treatment device 2 is configured in particular as an acute dialysis machine or an acute dialysis device and is thus essentially prepared for use in intensive care units with predominantly unstable patients. With the blood treatment device 2 of the present disclosure, princi-pally a variety of different blood treatment therapies can be performed (e.g. slow continuous ultrafiltration (SCUF), con-tinuous veno-venous hemofiltration (CVVH), continuous veno-venous hemodialysis (CVVHD), continuous veno-ve-nous hemodiafiltration (CVVHDF), therapeutic plasma exchange (TPE), etc.) as well as dilution modes (e.g., pre-dilution, post-dilution, pre-dilution and post-dilution) and anticoagulation types (e.g., none, heparin, citrate, etc.).

The blood treatment device 2 basically has an extracor-poreal circuit 4, a dialyzer (hemofilter) 6 and a dialysis fluid circuit 8 including a liquid feeding portion and a liquid draining portion. The extracorporeal circuit 4 and the dialy-sis fluid circuit 8 are separated by a membrane 10 provided in the dialyzer 6, through which blood can be filtered using a dialysis fluid solution or without using a dialysis fluid solution.

The extracorporeal circuit 4 comprises an arterial portion 12 and a venous portion 14. In principle, it is provided that the arterial portion 12, in particular one end thereof, is to be connected or attached to an artery of a patient, in particular an intensive care patient. It is also provided that the venous portion 14, in particular one end thereof, is to be connected or attached to a vein of a patient, in particular an intensive care patient.

The arterial portion 12 has, starting from an arterial end 16 in a blood flow direction towards the dialyzer 6, an arterial pressure sensor 18, an (arterial) blood pump 20, and a dialyzer inlet pressure sensor 22. Starting from the dialyzer 6 in a blood flow direction towards a venous end 24, the venous portion 14 has a venous expansion chamber or air trap 26, a safety air detector 28 and a safety valve 30. A venous pressure can be measured on/behind the venous expansion chamber 26 using a venous pressure sensor 32. Upstream of the (arterial) blood pump 20 a fluid line 80 merges into the end 16 of the arterial portion. The fluid line 80 in which a citrate pump 78 is arranged is connected to a bag 82 in which citrate is contained serving as an antico-agulation liquid. At bag 82 a load cell 84 is attached so that its weight can be continuously monitored, which is indicated by load cell line (dotted lines) 86 leading to a control unit (CPU) 68.

As shown in FIG. 6, the venous expansion chamber 26 is connected to a substitution solution bag/container 34. A substitution solution pump 36 is provided and configured to pump a substitution solution from the substitution solution bag 34 through fluid line 35 into the extracorporeal blood circuit 4, in particular into the venous portion 14 thereof (into the venous expansion chamber 26).

The dialysis fluid circuit 8 has at least one outlet 38 for effluent/used dialysis fluid (dialysate)/another fluid. In prin-ciple, the effluent/dialysate/the other liquid can flow through the outlet 38 from the dialyzer 6 to a collecting bag/container 40 for effluent/dialysate/etc. In the outlet 38, an effluent pressure sensor 42, a blood leak detector 44 and an effluent pump 46 are arranged or provided in a direction of flow from the dialyzer 6 to the collecting bag 40. The fluid line from pump 46 to the collecting bag 40 is designated by reference numeral 47.

As can be further seen in FIG. 6, a further bag/container 48 is provided in addition to the substitution solution bag 34 and the collecting bag 40. Depending on the desired blood treatment therapy to be performed, the bag 48 may contain, for example, a substitution solution/fluid or a dialysis fluid.

When, for example, a hemodialysis/hemodiafiltration treatment etc. is to be carried out with the extracorporeal blood treatment device 2, i.e. a blood treatment therapy in which dialysis fluid flows through the dialyzer 6 and thus a substance transport from the extracorporeal circuit 4 to the dialysis fluid circuit 8 takes place both by diffusion and convection, then the bag 48 contains dialysis fluid. When a first valve 50 is now opened and both a second valve 52 and a third valve 54 are closed, then the dialysis fluid can be pumped to the dialyzer 6 via a pump 56. The fluid line between pump 56 and bag 48 is designated with reference numeral 57.

When, for example, hemofiltration etc. is to be performed with the extracorporeal blood treatment device 2, i.e. a blood treatment therapy in which no dialysis fluid flows through the dialyzer 6 and thus substance transport from the extra-corporeal circuit 4 to the dialysis fluid circuit 8 takes place only via convection/filtration, the bag 48 can contain a substitution solution. When the first valve 50 and the second valve 52 are closed and the third valve 54 is opened, the substitution solution can be pumped from the bag 48 into the arterial portion 12 of the extracorporeal circuit 4 (pre-dilution). When the first valve 50 and the third valve 54 are closed and the second valve 52 is opened, the substitution solution can be pumped from the bag 48 into the venous portion 14 of the extracorporeal circuit 4 (post-dilution). According to the present disclosure, pre-dilution and post-dilution can also be achieved by pumping the substitution solution from the substitution solution bag 34 via the sub-stitution solution pump 36 into the venous portion 14 of the extracorporeal circuit 4 (post-dilution) and simultaneously pumping the substitution solution from the bag 48 via the pump (substitution solution pump) 56 into the arterial por-tion 12 of the extracorporeal circuit 4 (pre-dilution).

As shown in FIG. 6, a fluid warmer 58 and a pressure sensor 60 are provided between the pump 56 and the valve assembly consisting of the first valve 50, the second valve 52, and the third valve 54.

Like the citrate bag 82 also the three further bags, i.e. the substitution solution bag 34, the collecting bag 40 and the bag 48, each have load cells attached to them, namely a first load cell 62, a second load cell 64 and a third load cell 66. The first load cell 62 is basically configured to measure or monitor the weight of the substitution solution bag 34. The second load cell 64 is basically configured to measure or monitor the weight of the collecting bag 40. The third load cell 66 is basically configured to measure or monitor the weight of the bag 48. The load cells 62, 64, 66 and are basically examples of weighing devices. The present disclo-sure is not limited to the fact that the weighing devices are designed as load cells 62, 64, 66. Basically, any other weighing device/scale/force transducer can also be pro-vided, as long as it enables the weight/mass of a bag to be measured or monitored.

The extracorporeal blood treatment device 2 furthermore has a control unit (CPU) 68, which receives information from the sensors provided in the blood treatment device 2 and which controls the actuators provided in the blood treatment device 2. According to the disclosure, this pro-vides software-supported therapy in particular. The control unit 68 receives in particular information from the arterial pressure sensor 18, the dialyzer inlet pressure sensor 22, the safety air detector 28, the venous pressure sensor 32, the effluent pressure sensor 42, the blood leak detector 44, the pressure sensor 60, the first load cell 62, the second load cell 64, the third load cell 66, the fourth load cell 84, etc. The control unit 68 controls in particular the blood pump 20, the safety valve 30, the substitution solution pump 36, the effluent pump 46, the citrate pump 78 the first valve 50, the second valve 52, the third valve 54, the pump 56, the fluid warmer 58, etc. Pump control lines between the control unit 68 and the pumps 20, 36, 46, 56 and 78 are designated with reference numerals 88. Furthermore, the control unit 68 exchanges information with a user interface 70 designed as a display with touch screen. For example, the control unit 68 may be configured to display a warning or an alarm on the user interface 70. Furthermore, information entered by a user/operator on the user interface 70 can be transferred to the control unit 68.

The system of FIG. 6 thus has five CPU-controlled pumps 20, 36, 46, 56 and 78 which are connected through feed lines 80, 35, 47 and 57 to containers 82, 34, 40 and 48 for anticoagulation liquids, dialysate, substitution liquids and Effluents.

Pump 78 is a citrate pump and the appertaining container C is a bag 82 for an anticoagulation agent, such as citrate, equipped with a load cell 84. By applying the above-described leakage detection method, leakage can be detected from bag 82 and in the feed line 80 from bag 82 to pump 78 wherein any changed fluid delivery capability of the pump 78 is observable.

Pump 36 is a substitution solution pump 36 provided and configured to pump a substitution solution from the substitution solution bag 34 through fluid line 35 into the extracorporeal blood circuit 4. By applying the above-described leakage detection method leakage can be detected from container/bag 34, on feed line 35 between container 34 and pump 36, and the changed fluid delivery capability of pump 36 is observable.

Pump 46 is an effluent pump 46 arranged or provided in a direction of flow from the dialyzer 6 to the collecting bag 40. The fluid line from pump 46 to the collecting bag 40 is designated by reference numeral 47. By applying the above-described leakage detection method, leakage can be detected from container 40 and in feed line 47 between pump 46 and container 40, wherein the changed fluid delivery capability of pump 46 is observable.

Moreover, pump 56 can be a dialysis fluid pump and the container C is a dialysis fluid bag 48 equipped with load cell 66. The fluid line from container or bag 48 to pump 56 is designated by reference numeral 57. By applying the above-described leakage detection method, leakage can be detected from container 40 and in feed line 57 between container 48 and pump 56, wherein the changed fluid delivery capability of pump 56 is observable.

It becomes clear from the above, that in the acute dialysis machine the proposed method can be used to detect fluid leakage by measuring weight and rotation without the need of the application of a HW-based leakage detector equipment. The method is suitable for detecting leakage on lines that connect pumps and fluid containers including Anticoagulation, Dialysate, Substitution and Effluent line, i.e. to any hydraulic circuit unit HCU as above described. Detection of leakage from the containers is also possible as well as the changed fluid delivery capability of the pumps via this method.

Various modifications of the leakage detection system are possible without leaving the basic concept of the disclosure. For example, instead of weight detectors (load cells) it is also possible to calculate the values of filling degree change rates by detecting only the filling level of the bags. The change rate of fluid in the bags can then be calculated by applying the geometric data of the container.

The application of the described leakage detection method is not restricted to specific pumps, e.g. peristaltic pumps. Preferably, the system uses pumps which have exact delivery rates that do not change when the speed is kept constant.

The described method can also be applied in systems in which more than one pump are connected to more than one container. Here, the summed-up flow rate induced by the pumps is taken as the basis for calculating the expected weight change rate and the summed-up monitored changes rates of the weight of the containers is continuously compared with the expected change rate.

In short, the present disclosure relates to a leakage detection method in fluid containing or transporting disposables, such as containers, lines or cartridges, in particular in medical disposables to be used in blood treatment devices for e.g. blood treatment therapies, in which at least one pump controlled by a control unit (CPU) is connected through at least one fluid feed line to at least one container and the filling degree, e.g. the weight of said container is continuously monitored. For allowing quick, easy and accurate leakage detection with a minimum of structural modifications of a fluid circuit unit consisting of pump, feed line and container, the method has the steps of:

calculating or determining a flow rate in said at least one fluid feed line based on the current performance of the at least one pump and optionally on selected characteristics of the hydraulic system including pump, feed line and container, either calculating or determining an expected change rate value of the filling degree (weight) of said at least one container based on said calculated at least one flow rate, or setting the expected change rate value as a previous value of a monitored change rate (CR) of the filling degree (weight) of said at least one container, continuously monitoring a deviation value between said expected change rate value and a continuously monitored change rate of the filling degree (weight) of said at least one container and detecting leakage based on said deviation value.

Moreover, the present disclosure relates to a leakage detection system of fluid containing or transporting disposables, such as containers, lines or cartridges, in particular of medical disposables in particular for use in blood treatment devices for e.g., blood treatment therapies, which—for carrying out the leakage detection method—, is equipped with calculation/determination modules (CPU) configured to calculate/determine the flow rate (RF) in said at least one fluid feed line and to calculate/determine an expected change rate value of the filling degree (weight) of said at least one container based on said calculated at least one flow rate. Moreover, it has an evaluation module (CPU) configured to continuously monitor the deviation value between said expected change rate value and a continuously monitored change rate of the filling degree of said at least one container, and output means configured to output a leakage signal based on said deviation value.

What is claimed:

1. A leakage detection method in fluid-containing or fluid-transporting disposables, the method comprising the steps of:

connecting at least one pump controlled by a control unit through at least one fluid feed line to at least one container;

continuously monitoring a filling degree of the at least one container;

calculating or determining a flow rate in the at least one fluid feed line based on a current performance of the at least one pump;

establishing an expected change rate value of the filling degree of the at least one container by either:

calculating or determining expected change rate value based on the at least one flow rate, or setting the expected change rate value as a previous value of a monitored change rate of the filling degree of the at least one container;

continuously monitoring a deviation value between the expected change rate value and a monitored change rate of the filling degree of the at least one container with the control unit; and detecting a leakage based on the deviation value.

2. The leakage detection method according to claim 1, wherein the filling degree of the at least one container is monitored by continuously measuring a weight of the at least one container.

3. The leakage detection method according to claim 1, wherein the step of calculating or determining the flow rate in the at least one fluid feed line further comprises the step of calculating or determining the flow rate based on selected characteristics of a hydraulic system including the at least one pump, the at least one fluid feed line, and the at least one container.

4. The leakage detection method according to claim 1, wherein a leakage signal is output when the deviation value is for a pre-determined time interval above a pre-determined threshold value.

5. A leakage detection system for fluid-containing or fluid-transporting disposables, the leakage detection system comprising:

at least one pump which is controlled by a control unit and which is connected through at least one fluid feed line to at least one container;

a filling degree monitoring device configured to continuously monitor and report a filling degree of the at least one container to the control unit;

a first calculation/determination module configured to calculate a flow rate in the at least one fluid feed line based on a current performance of the at least one pump;

a second calculation/determination module configured to calculate an expected change rate value of the filling degree of the at least one container based on the at least one flow rate;

an evaluation module configured to continuously monitor a deviation value between the expected change rate value and a monitored change rate of the filling degree of the at least one container; and output means configured to output a leakage signal based on the deviation value.

6. The leakage detection system according to claim 5, wherein the filling degree monitoring device is configured to continuously measure a weight of the at least one container.

7. The leakage detection system according to claim 5, wherein the first calculation/determination module is further configured to calculate the flow rate in the at least one fluid feed line based on selected characteristics of a hydraulic system including the at least one pump, the at least one feed line and the at least one container.

8. The leakage detection system according to claim 5, wherein the output means is configured to output a leakage signal when the deviation value is for a pre-determined time interval above a pre-determined threshold value.

9. The leakage detection system according to claim 5, wherein the at least one pump comprises a plurality of pumps, and the plurality of pumps is connected to the at least one container.

10. The leakage detection system according to claim 5, wherein the at least one container comprises a plurality of containers, and the at least one pump is connected to the plurality of containers.

11. The leakage detection system according to claim 5, wherein the leakage detection system is integrated in an acute dialysis machine and features one of the following:

a) the at least one pump is a citrate pump and the at least one container is a citrate bag equipped with a load cell; or b) the at least one pump is a substitution solution pump and the at least one container is a substitution solution bag equipped with a load cell; or c) the at least one pump is an effluent pump and the at least one container is an effluent collecting bag equipped with a load cell; or d) the at least one pump is a dialysis fluid pump and the at least one container is a dialysis fluid bag equipped with a load cell.

12. A leakage detection method in fluid-containing or fluid-transporting disposables, the method comprising the steps of:

connecting at least one pump controlled by a control unit through at least one fluid feed line to at least one container;

continuously monitoring a filling degree of the at least one container;

calculating or determining a flow rate in the at least one fluid feed line based on a current performance of the at least one pump;

establishing an expected change rate value of the filling degree of the at least one container by either:

calculating or determining expected change rate value based on the at least one flow rate, or setting the expected change rate value as a previous value of a monitored change rate of the filling degree of the at least one container;

continuously monitoring a deviation value between the expected change rate value and a monitored change rate of the filling degree of the at least one container with the control unit; and detecting a leakage based on the deviation value, wherein the step of calculating or determining the flow rate in the at least one fluid feed line further comprises the step of calculating or determining the flow rate based on selected characteristics of a hydraulic system including the at least one pump, the at least one fluid feed line, and the at least one container, and wherein the selected characteristics of the hydraulic fluid system include data relating to at least one influence input out of a group of energy losses over fluid speed, mechanical parameters of the pump over pump performance and on hydrostatic pressure at a connection port of the pump.

13. The leakage detection method according to claim 12, wherein the data relating to the at least one influence input are taken from a look-up-table based on measured and/or calculated characteristics of the hydraulic system including the at least one pump, the at least one fluid feed line and the at least one container.

14. A leakage detection system for fluid-containing or fluid-transporting disposables, the leakage detection system comprising:

at least one pump which is controlled by a control unit and which is connected through at least one fluid feed line to at least one container;

a filling degree monitoring device configured to continuously monitor and report a filling degree of the at least one container to the control unit;

a first calculation/determination module configured to calculate a flow rate in the at least one fluid feed line based on a current performance of the at least one pump;

a second calculation/determination module configured to calculate an expected change rate value of the filling degree of the at least one container based on the at least one flow rate;

an evaluation module configured to continuously monitor a deviation value between the expected change rate value and a monitored change rate of the filling degree of the at least one container; and output means configured to output a leakage signal based on the deviation value, wherein the first calculation/determination module is further configured to calculate the flow rate in the at least one fluid feed line based on selected characteristics of a hydraulic system including the at least one pump, the at least one feed line and the at least one container, and wherein the selected characteristics of the hydraulic system include data relating to at least one influence input out of a group of energy losses over fluid speed, mechanical parameters of the at least one pump over pump performance and on hydrostatic pressure at a connection port of the at least one pump.

15. The leakage detection system according to claim 14, wherein the data relating to the at least one influence input are taken from a look-up-table based on measured and/or calculated characteristics of the hydraulic system including the at least one pump, the at least one feed line and the at least one container.

16. A leakage detection system for fluid-containing or fluid-transporting disposables, the leakage detection system comprising:

at least one pump which is controlled by a control unit and which is connected through at least one fluid feed line to at least one container;

a filling degree monitoring device configured to continuously monitor and report a filling degree of the at least one container to the control unit;

a first calculation/determination module configured to calculate a flow rate in the at least one fluid feed line based on a current performance of the at least one pump;

a second calculation/determination module configured to calculate an expected change rate value of the filling degree of the at least one container based on the at least one flow rate;

an evaluation module configured to continuously monitor a deviation value between the expected change rate value and a monitored change rate of the filling degree of the at least one container; and output means configured to output a leakage signal based on the deviation value, wherein:

the at least one container comprises a filling level detector configured to report a filling level signal to the control unit, and the filling level signal is used to compensate an influence of changes of hydrostatic pressure present at a connection port of the at least one pump with the at least one fluid feed line when calculating an expected weight change value.

* * * * *